United States Patent
Hui et al.

(10) Patent No.: US 10,258,294 B2
(45) Date of Patent: Apr. 16, 2019

(54) ALARM CONTROLLING METHOD AND APPARATUS FOR PATIENT MONITOR, AND ADAPTIVE ALARMING METHOD FOR PATIENT MONITOR

(71) Applicant: GENERAL ELECTRIC COMPANY, Schenectady, NY (US)

(72) Inventors: Hui Hui, Jiangsu (CN); Lu Liu, Jiangsu (CN); Lei Zheng, Jiangsu (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/791,727

(22) Filed: Oct. 24, 2017

(65) Prior Publication Data

US 2018/0110476 A1 Apr. 26, 2018

(30) Foreign Application Priority Data

Oct. 26, 2016 (CN) .......................... 2016 1 0948479

(51) Int. Cl.
*G06F 19/00* (2018.01)
*A61B 5/00* (2006.01)
*G16H 40/63* (2018.01)
*G06Q 50/22* (2018.01)

(52) U.S. Cl.
CPC .............. *A61B 5/746* (2013.01); *A61B 5/747* (2013.01); *G16H 40/63* (2018.01); *A61B 5/0002* (2013.01); *G06F 19/3418* (2013.01); *G06Q 50/22* (2013.01)

(58) Field of Classification Search
CPC .... G08B 29/185; G08B 21/182; G08B 21/02; G05B 23/0262; G06F 11/079; G06F 19/3418; A61B 5/0002; A61B 5/746; A61B 5/747
See application file for complete search history.

(56) References Cited

U.S. PATENT DOCUMENTS

| 2007/0213599 | A1* | 9/2007 | Siejko | A61B 5/00 600/300 |
| 2010/0016691 | A1* | 1/2010 | Watson | A61B 5/14551 600/323 |
| 2010/0222653 | A1* | 9/2010 | Siejko | A61B 5/00 600/301 |
| 2011/0307743 | A1* | 12/2011 | Khalak | G05B 23/0262 714/47.2 |
| 2013/0237775 | A1* | 9/2013 | Gross | A61B 5/0205 600/301 |
| 2017/0069198 | A1* | 3/2017 | Kwon | G08B 29/185 |
| 2017/0124855 | A1* | 5/2017 | Kang | G08B 29/185 |

\* cited by examiner

*Primary Examiner* — Mirza F Alam (57) ABSTRACT

The present invention provides an alarm controlling method, an alarm controlling apparatus and an adaptive alarming method for a patient monitor. The alarm controlling method comprises: acquiring false alarm probabilities of a plurality of current alarms; acquiring a corresponding alarm confidence according to a false alarm probability of each current alarm; and determining a priority of the current alarm based on at least the alarm confidence of the current alarm.

15 Claims, 6 Drawing Sheets

ALARM CONTROLLING METHOD AND APPARATUS FOR PATIENT MONITOR, AND ADAPTIVE ALARMING METHOD FOR PATIENT MONITOR

CROSS REFERENCE

This application claims priority to Chinese application number 201610948479.0, filed Oct. 26, 2016, which is incorporated herein by reference.

FIELD

The present invention relates to the field of medical monitoring, particularly to an alarm controlling method and apparatus for a patient monitor, and a self-adaptive alarming method for a patient monitor.

BACKGROUND

It is well known that a patient monitor may measure various physiological parameters of a patient, and can send out a corresponding alarm when the measured parameter is abnormal, so as to achieve real-time monitoring for the patient and emergency treatment by a medical staff. However, the patient monitor may also present an error alarm, i.e., a false alarm. The existence of the false alarm may make the medical staff give a wrong judgment of the patient's monitoring, so as to put the patient in a potential risk.

The patient monitor generally displays alarm information in a fixed display area according to alarm levels. For example, when an alarm level is "high", it is displayed with a high priority. In this way, when high-level alarm information is displayed with a high priority in the limited display area, which is actually a false alarm, a response made by the medical staff to it on the one hand causes a waste of clinical resources, and on the other hand may cause a real emergency alarm not being displayed. Also, displaying the false alarm in a long-term will cause fatigue of the medical staff to the alarm, so that patients cannot get timely care.

SUMMARY

One objective of the present invention is to provide an alarm controlling method and apparatus for a patient monitor, and a self-adaptive alarming method for the patient monitor, so as to improve an accuracy of a priority of an alarm, reduce a waste of clinical resources caused by a false alarm and reduce a risk to a patient caused by the false alarm.

An exemplary embodiment of the present invention provides an alarm controlling method for a patient monitor, comprising: acquiring false alarm probabilities of a plurality of current alarms; acquiring a corresponding alarm confidence based on a false alarm probability of each current alarm; and determining a priority of the current alarm based on at least the alarm confidence of the current alarm.

An exemplary embodiment of the present invention further provides a self-adaptive alarming method for a patient monitor, comprising: accumulating current alarm times and false alarm times of a current alarm into a historical alarm number and a historical false alarm number in historical alarm data respectively so as to obtain updated historical alarm data; acquiring a false alarm probability of the current alarm in the updated historical alarm data according to a ratio of the historical false alarm number to the historical alarm number of the current alarm; acquiring an alarm confidence of the current alarm based on the false alarm probability of the current alarm, so as to determine a priority of the current alarm based on at least the alarm confidence of the current alarm when the current alarm occurs again.

An exemplary embodiment of the present invention further provides an alarm controlling apparatus for a patient monitor, comprising: a probability-of-false-alarm acquisition module, an alarm confidence acquisition module and a priority determination module, wherein the probability-of-false-alarm acquisition module is used for acquiring false alarm probabilities of a plurality of current alarms; the alarm confidence acquisition module is used for acquiring a corresponding alarm confidence based on a false alarm probability of each current alarm; the priority determination module is used for determining a priority of the current alarm based on at least the alarm confidence of the current alarm.

Other features and aspects will be apparent through the following detailed description, figures and claims.

BRIEF DESCRIPTION OF THE DRAWINGS

The present invention can be better understood in light of the description of exemplary embodiments of the present invention with reference to the accompanying drawings, in which.

DETAILED DESCRIPTION

Hereafter, a detailed description will be given for preferred embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for one of ordinary skilled in the art associated with the contents disclosed in the present disclosure, which should not be regarded as insufficient disclosure of the present disclosure.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present application for invention do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

Figure 1:
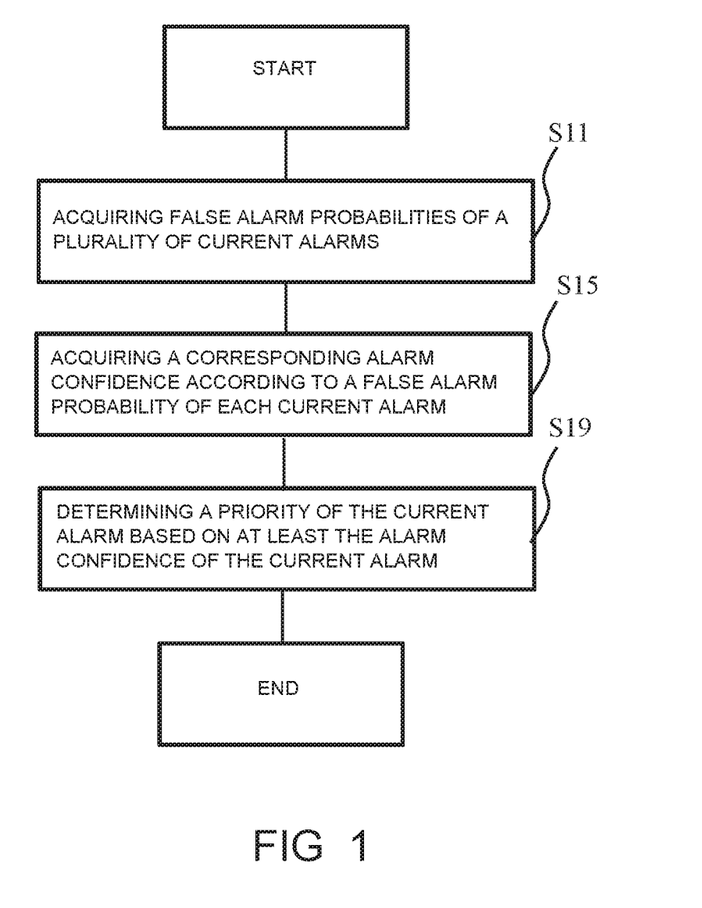
FIG. 1 is a flowchart of an alarm controlling method for a patient monitor provided by one embodiment of the present invention.
Figure 2:
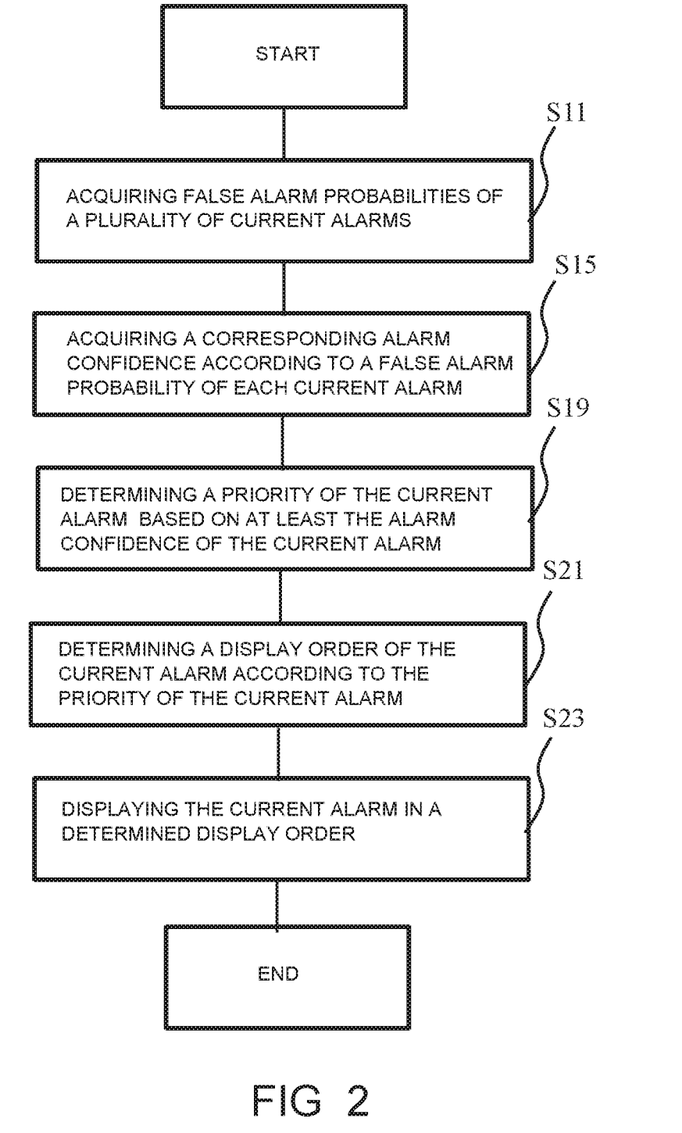
FIG. 2 is a flowchart of an alarm controlling method for a patient monitor provided by another embodiment of the present invention.

FIG. 1 is an alarm controlling method for a patient monitor provided by an embodiment of the present invention. In one embodiment, the method may be used for determining a priority of an alarm of a patient monitor, so that an alarm with a high confidence can be displayed in an alarm display area of a patient monitor. FIG. 2 is one example of an alarm display area of a patient monitor provided by an embodiment of the present invention.

FIG. 1 is a flowchart of an alarm controlling method for a patient monitor provided by one embodiment of the present invention. As shown in FIG. 1, the alarm controlling method for a patient monitor provided by the embodiment of the present invention comprises the following Steps S11, S15 and S19.

In Step S11, false alarm probabilities of a plurality of current alarms are acquired. The "plurality of current alarms" described above may comprise multiple physiological conditions obtained by the patient monitor through physiological monitoring for a patient, for example, which may comprise Tachy, Brady, V-Fib, Asystole, SpO2 High, SpO2 Low, RESP Low and the like. The "false alarm" described above may be understood as an error alarm of one or more of the physiological conditions.

In Step S11, by determining a ratio of false alarm number to alarm number of each current alarm in historical alarm data, a false alarm probability of each current alarm may be obtained.

For example, in the historical alarm data, every time when an alarm occurs, the alarm is accumulated. If the alarm is determined as a false alarm, its false alarm is accumulated, so that the historical alarm data is continuously updated. Then in Step S11, when a false alarm probability of each alarm needs to be acquired, by acquiring a ratio of the accumulated number of the false alarm to the corresponding accumulated number of the alarm, a corresponding false alarm probability can be obtained. Take an alarm for Tachy as an example to illustrate. Assuming that the alarm number for Tachy is N and false alarm number for Tachy is M in the historical alarm data, for the alarm for Tachy, its false alarm probability in the historical alarm data is M/N.

In Step S15, a corresponding alarm confidence is acquired according to the false alarm probability of each current alarm. In Step S19, a priority of the current alarm is determined based on at least the alarm confidence of the current alarm.

For example, if current alarms for the patient monitor include Brady, V-Fib, SpO2 Low and RESP Low and in the historical alarm data, a false alarm probability of an alarm for Brady is 20%, a false alarm probability of an alarm for V-Fib is 60%, a false alarm probability of an alarm for SpO2 Low is 45%, and a false alarm probability of an alarm for RESP Low is 80%, alarm confidences for the alarms described above may be arranged from high to low as: the alarm for Brady (a false alarm rate of 20%), the alarm for SpO2 Low (a false alarm rate of 45%), the alarm for V-Fib (a false alarm rate of 60%), and the alarm for RESP Low (a false alarm rate of 80%). Then in Step S19, a priority for each current alarm may be determined in the above order. That is, the higher the alarm confidence is, the higher the priority is.

The "at least" in "a priority of the current alarm is determined based on at least the alarm confidence of the current alarm" described above may be understood as: a priority of the current alarm may be further determined based on other information at the same time. The other information may be, for example, an alarm level of each alarm itself (the alarm level that has been already determined in the prior art). In one embodiment, a priority of the alarm level for the alarm itself may be kept unchanged, while its priority is adjusted only for the alarm confidence with the same alarm level.

For example, the "plurality of current alarms" described above may have a plurality of alarm levels. For the current alarm with the same alarm level, a priority of the current alarm rises as its alarm confidence increases.

For example, an alarm for Asystole and the alarm for RESP Low may be set at the same level (e.g., a higher level), while the alarm for Brady and the alarm for V-Fib may be set at another level (e.g., a lower level). In the current alarm, for the alarms for Asystole and RESP Low at the same level, if the false alarm rate of the alarm for Asystole is greater than the false alarm rate of the alarm for RESP Low, an alarm confidence of the alarm for Asystole is less than an alarm confidence of the alarm for RESP Low. When the current alarm is displayed, the alarm for RESP Low is displayed with a high priority. But, if an alarm confidence of the alarm for Brady is higher than the alarm confidence of the alarm for Asystole, according to the alarm levels of the alarms themselves, the alarm for Asystole is still displayed with a high priority.

Certainly, in other embodiments, in the situation where the acquired alarm confidences are accurate enough, it may also be considered that firstly a priority of the alarm is determined according to the alarm confidence, and then the priority of the alarm is determined according to the alarm levels of the alarms themselves.

The "historical alarm data" described above may be stored in the patient monitor or in a workstation or a back-end server in communication with the patient monitor. When the "historical alarm data" is stored in the workstation or the back-end server, it means that the workstation or the back-end server may receive alarm information from a plurality of patient monitors (e.g., all the patient monitors connected to the workstation or the back-end server) and analyze the alarm information. Thus, alarm confidences and priorities of various alarms are determined in the manner of big data. For example, when patient monitors of the same model or the same product batch are connected to the workstation or the back-end server, alarm confidences and priorities of current alarms of the patient monitors may be acquired from the workstation or the back-end server.

FIG. 2 is a flowchart of an alarm controlling method for a patient monitor provided by another embodiment of the present invention. The embodiment is similar to the embodiment as shown in FIG. 1, and the difference is that after Step S19, Step S21 and Step S23 may further be comprised.

In Step S21, a display order of the current alarm is determined according to the priority of the current alarm. After the display order is determined in Step S21, the current alarm may be displayed in a determined display order in Step S23. For example, for the determined display order described above, the display order may be: the alarm for Brady, the alarm for SpO2 Low, the alarm for V-Fib and the alarm for RESP Low. If only three alarms are allowed to be displayed in the alarm display area of the patient monitor, the alarm for Brady (the false alarm rate of 20%), the alarm for SpO2 Low (the false alarm rate of 45%) and the alarm for V-Fib (the false alarm rate of 60%) are displayed in the display order, while the alarm for RESP Low with the lowest priority (lowest confidence) is not displayed.

Optionally, after Step S19, Step S25 may be further comprised: displaying the alarm confidence of the current alarm.

In one embodiment, while the current alarm is displayed, the corresponding false alarm rate may be displayed in the alarm display area of the patient monitor at the same time to reflect the alarm confidence. That is, the higher the false alarm rate is, the lower the alarm confidence is. In another embodiment, the alarm confidences may be classified into multiple levels. For example, for the false alarm rate of 0-25%, the trust is at a four-star level; and for the false alarm rates of 25%-50%, 50%-75% and 75%-100%, the trusts are at a three-star level, a two-star level and a one-star level respectively. While the current alarm is displayed, the level of the corresponding alarm confidence may be displayed in the alarm display area of the patient monitor at the same time. For example, for the above-described alarm for Brady, alarm for SpO2 Low, alarm for V-Fib and alarm for RESP Low, their corresponding alarm confidences may be displayed in the way as shown in the following Table 1:

TABLE 1

| Brady | SpO2 Low | V-Fib | RESP Low |
|---|---|---|---|
| ★★★★ | ★★★☆ | ★★☆☆ | ★☆☆☆ |

Figure 3:
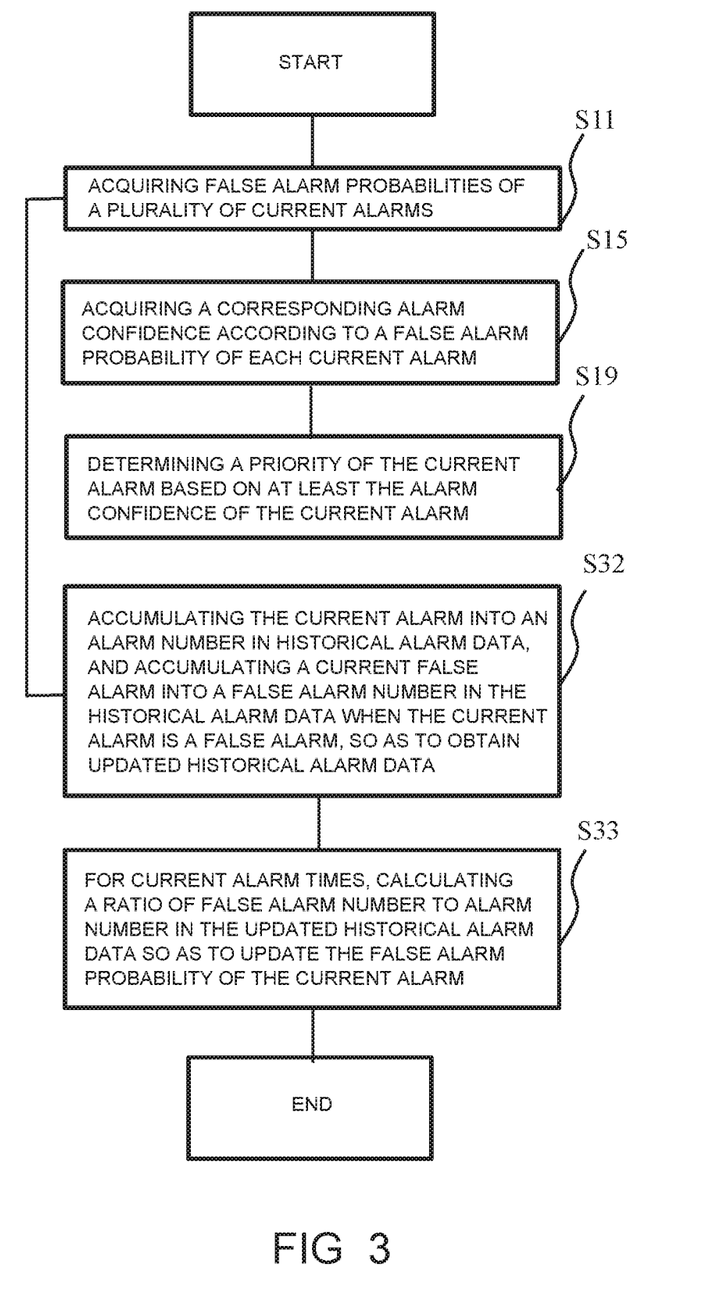
FIG. 3 is a flowchart of an alarm controlling method for a patient monitor provided by another embodiment of the present invention.

FIG. 3 is a flowchart of an alarm controlling method for a patient monitor provided by another embodiment of the present invention. As shown in FIG. 3, the embodiment is similar to the alarm controlling method for a patient monitor as shown in FIG. 1 or FIG. 2, and the difference is that in the embodiment as shown in FIG. 3, after Step S11, the following Steps S32 and S33 may further be comprised.

In Step S32, the current alarm is accumulated into the alarm number in the historical alarm data, and a current false alarm is accumulated into the false alarm number in the historical alarm data when the current alarm is a false alarm, so as to obtain an updated historical alarm data. Take the alarm for Tachy as an example to illustrate. Assuming that the alarm number for Tachy is N and the false alarm number for Tachy is M in the historical alarm data, if the current alarm includes Tachy and the alarm for Tachy is determined as a false alarm, the alarm times for Tachy is updated to N+1 and the false alarm times for Tachy is updated to M+1. If the current alarm includes Tachy and the alarm for Tachy is not a false alarm, the alarm times for Tachy is updated to N+1, but the false alarm times for Tachy remains the same, which is still M. In the above way, updating of the historical alarm data for the alarm for Tachy is carried out.

In Step S33, for current alarm, the ratio of the false alarm number to the alarm number in the updated historical alarm data is calculated so as to update the false alarm probability of the current alarm. Still take the above alarm for Tachy as an example to illustrate. Assuming that the alarm number for Tachy is N and the false alarm number for Tachy is M in the historical alarm data, a false alarm probability of the alarm for Tachy in the historical alarm data is "M/N." If the current alarm includes Tachy and it is a false alarm, by acquiring a ratio of updated false alarm number for Tachy "M+1" to updated alarm number for Tachy "N+1" as a false alarm ratio of the alarm for Tachy "(M+1)/(N+1)", updating of the false alarm probability of the alarm for Tachy is carried out.

Figure 4:
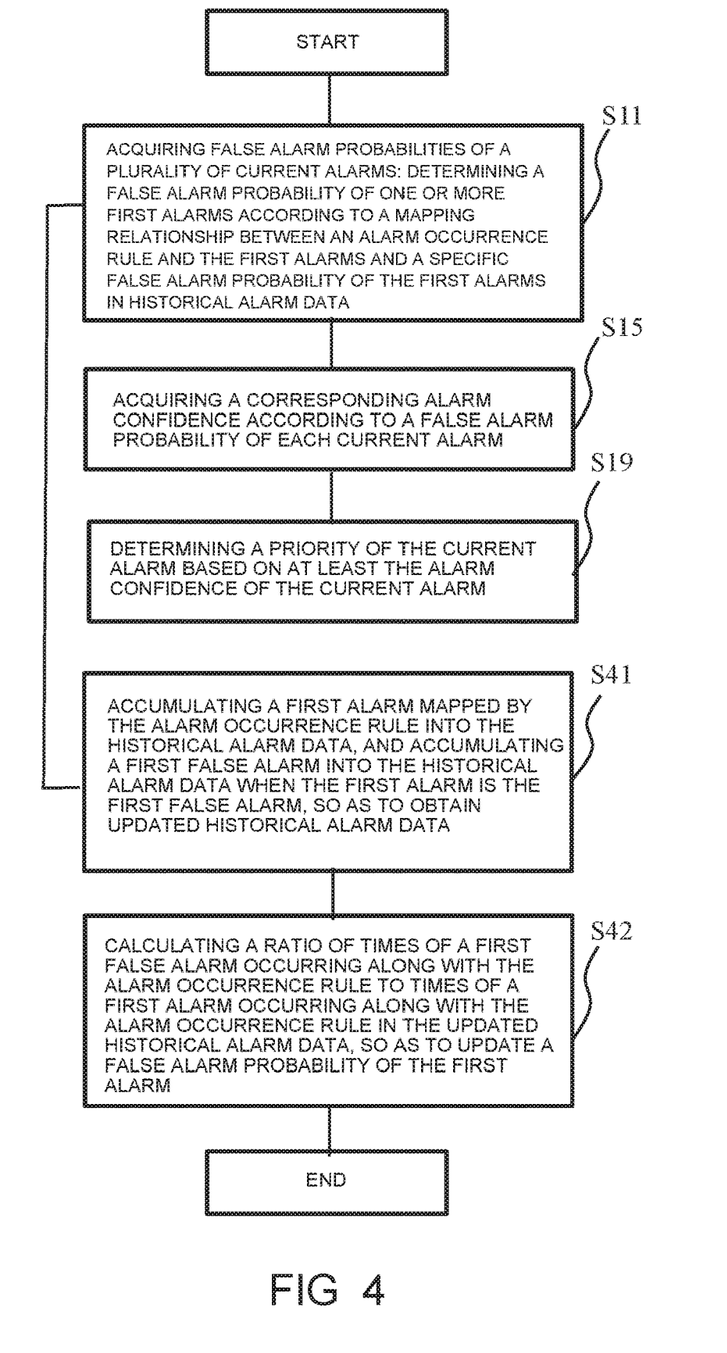
FIG. 4 is a flowchart of an alarm controlling method for a patient monitor provided by another embodiment of the present invention.

FIG. 4 is a flowchart of an alarm controlling method for a patient monitor provided by another embodiment of the present invention. The embodiment is similar to any one of the embodiments as shown in FIG. 1-FIG. 3, and the difference is that in Step S11, "acquiring false alarm probabilities of a plurality of current alarms" further comprises: determining a false alarm probability of one or more first alarms according to a mapping relationship between an alarm occurrence rule and the first alarms and a specific false alarm probability of the first alarms in the historical alarm data. The above first alarms may be any one or more of the "plurality of current alarms" described above, e.g., the alarm for Tachy. The number of the alarms that meet the above "alarm occurrence rule" may be one or more, which may include the above first alarms or may not include the above first alarms.

The "alarm occurrence rule" described above may comprise: at least two second alarms occur within a specific time interval (e.g., two seconds). The second alarms and the first alarms have the same or different names. For example, the second alarms may be Tachy, Brady and SpO2 Low.

Optionally, after Step S11, the following Steps S41 and S42 may further be comprised.

In Step S41, a first alarm mapped by the alarm occurrence rule is accumulated into the historical alarm data, and when the first alarm is a first false alarm, the first false alarm is accumulated into the historical alarm data, so as to obtain updated historical alarm data.

In Step S42, a ratio of times of a first false alarm occurring along with the alarm occurrence rule to times of a first alarm occurring along with the alarm occurrence rule in the updated historical alarm data is calculated, so as to update a false alarm probability of the first alarm.

For example, when the second alarms for Tachy, Brady and SpO2 Low occur within two seconds in the patient monitor, in the historical alarm data, according to a mapping relationship between the rule (the second alarms for Tachy, Brady and SpO2 Low occur within two seconds) and the alarm for SpO2 Low (as the first alarm at this moment) and its false alarm probability (e.g., 90%), a false alarm probability 90% for the first alarm for SpO2 Low may be acquired directly.

At this moment, it is assumed that alarm number of the first alarm for SpO2 Low mapped by the rule is N and its false alarm number is M (i.e., M/N=90%) in the historical alarm data. If the current first alarm for SpO2 Low is a false alarm, in Step 41, the alarm number of the first alarm for SpO2 Low mapped by the rule may be updated to N+1 and its false alarm number may be updated to M+1, and in Step S42, the false alarm rate of the first alarm for SpO2 Low mapped by the rule may be updated to (M+1)/(N+1); If the current first alarm for SpO2 Low is not a false alarm, in Step

41, the alarm number of the first alarm for SpO2 Low mapped by the rule is updated to N+1 and its false alarm number remains the same, which is still M, and in Step S42, the false alarm rate of the first alarm for SpO2 Low mapped by the rule is updated to M/(N+1).

By updating the historical alarm data and the false alarm rate of the current alarm, it is convenient to determine its alarm confidence when the current alarm occurs next time, so as to determine its alarm priority.

Figure 5:
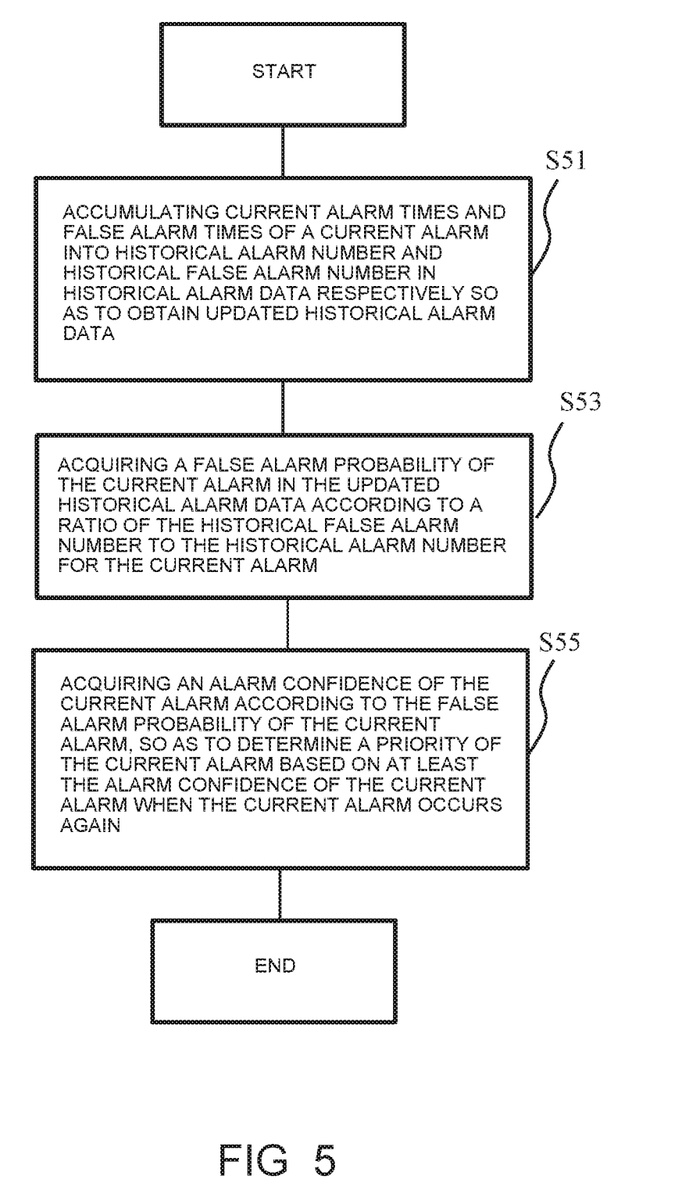
FIG. 5 is a flowchart of a self-adaptive alarming method for a patient monitor provided by one embodiment of the present invention.

According the above description, an embodiment of the present invention may further provide a self-adaptive alarming method for a patient monitor. FIG. 5 shows a flowchart of the method. As shown in FIG. 5, the adaptive alarming method for a patient monitor comprises Steps S51, S53 and S55.

In Step S51, current alarm times and false alarm times of a current alarm are accumulated into a historical alarm number and a historical false alarm number in historical alarm data respectively, so as to obtain updated historical alarm data.

In Step S53, a false alarm probability of a current alarm is acquired in the updated historical alarm data according to a ratio of the historical false alarm number to the historical alarm number of the current alarm.

In Step S55, an alarm confidence of the current alarm is acquired according to the false alarm probability of the current alarm, so as to determine a priority of the current alarm at least according to the alarm confidence of the current alarm when the current alarm occurs again.

The data updating (including the historical alarm number, the historical false alarm number and the false alarm probability) for the "current alarm" mentioned in the present embodiment may be updating made for the alarm that is only regarded as a separate individual or may also be updating made for the alarm mapped by (conforming to) a specific alarm occurrence rule, which have been described in details in the embodiments as shown in FIG. 3 and FIG. 4.

Based on this, in Step 53, the adaptive alarming method for a patient monitor in the present embodiment may further comprise the following steps:

if the current alarm conforms to the specific alarm occurrence rule, acquiring the historical alarm number and the historical false alarm number of the current alarm which conforms to the specific alarm occurrence rule in the updated historical alarm data; and calculating a ratio of the historical false alarm number to the historical alarm number of the current alarm which conforms to the specific alarm occurrence rule, so as to acquire the false alarm probability of the current alarm which conforms to the specific alarm occurrence rule.

Figure 6:
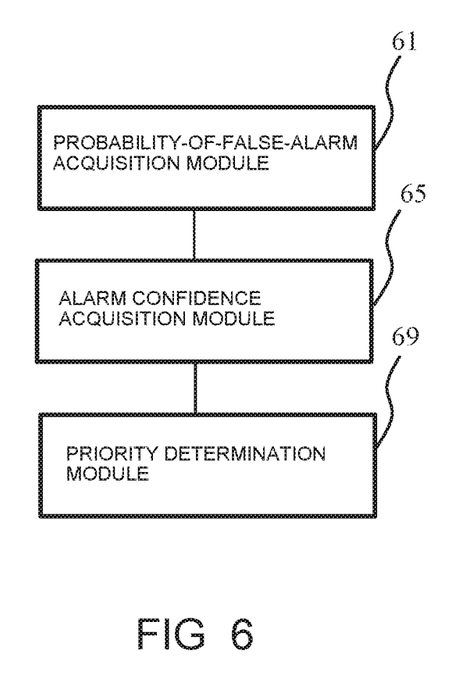
FIG. 6 is a flowchart of an alarm controlling apparatus for a patient monitor provided by one embodiment of the present invention.

FIG. 6 is a block diagram of an alarm controlling apparatus for a patient monitor provided by one embodiment of the present invention. The alarm controlling apparatus may be provided in a patient monitor or in a workstation or a back-end server connected to the patient monitor.

The alarm controlling apparatus may be used to perform the alarm controlling method in the above embodiments. As shown in FIG. 6, the alarm controlling apparatus may comprise a probability-of-false-alarm acquisition module 61, an alarm confidence acquisition module 65 and a priority determination module 69.

The probability-of-false-alarm acquisition module 61 is used for acquiring false alarm probabilities of a plurality of current alarms. The alarm confidence acquisition module 65 is used for acquiring a corresponding alarm confidence according to a false alarm probability of each current alarm. The priority determination module 69 is used for determining a priority of the current alarm based on at least the alarm confidence of the current alarm.

Optionally, the alarm controlling apparatus may further comprise a display order determination module and a display module. The display order determination module is used for determining a display order of the current alarm according to the priority of the current alarm. The display module is used for displaying the current alarm in a determined display order.

Optionally, the display module described above is also used for displaying the alarm confidence of the current alarm.

Optionally, the above plurality of current alarms have a plurality of alarm levels. For the alarm with the same alarm level, a priority of the alarm rises as its alarm confidence increases.

Optionally, the probability-of-false-alarm acquisition module described above is used for determining a ratio of false alarm number to alarm number of each current alarm in historical alarm data, so as to obtain a false alarm probability of each current alarm.

Optionally, the alarm controlling apparatus for a patient monitor in the embodiment of the present invention further comprises a first historical data updating module and a first probability-of-false-alarm updating module.

The first historical data updating module is used for accumulating the current alarm into the alarm number in the historical alarm data, and accumulating a current false alarm into the false alarm number in the historical alarm data when the current alarm is a false alarm, so as to obtain updated historical alarm data.

The first probability-of-false-alarm updating module is used for calculating a ratio of false alarm number to alarm number in the updated historical alarm data for current alarm, so as to update the false alarm probability of the current alarm.

Optionally, the probability-of-false-alarm acquisition module described above may be further used for determining a false alarm probability of one or more first alarms according to a mapping relationship between an alarm occurrence rule and the first alarms and a false alarm probability of the first alarms in the historical alarm data.

Optionally, the alarm occurrence rule described above may comprise: at least two second alarms occur within a specific time interval. The second alarms and the first alarms have the same or different names.

Optionally, the alarm controlling apparatus for a patient monitor in the embodiment of the present invention may further comprise a second historical data updating module and a second probability-of-false-alarm updating module.

The second historical data updating module is used for accumulating a first alarm mapped by the alarm occurrence rule into the historical alarm data, and accumulating a first false alarm into the historical alarm data when the first alarm is the false alarm, so as to obtain the updated historical alarm data.

The second probability-of-false-alarm updating module is used for calculating a ratio of times of a first false alarm occurring along with the alarm occurrence rule to times of a first alarm occurring along with the alarm occurrence rule in the updated historical alarm data, so as to update a false alarm probability of the first alarm.

When the alarm controlling apparatus for a patient monitor in the embodiment of the present invention is provided in the workstation or the back-end server, the probability-of-false-alarm acquisition module 61 described above is used for acquiring false alarm probabilities of the plurality of current alarms from a plurality of patient monitors.

When a current alarm occurs in a patient monitor, an alarm confidence and priority of the current alarm may be acquired from the workstation or the back-end server, and a display order of the current alarm is acquired from the workstation or the back-end server for displaying.

The embodiments of the present invention provide an alarm controlling method, an alarm controlling apparatus and an adaptive alarming method for a patient monitor, which can determine an alarm confidence of a current alarm by acquiring its false alarm probability, and determine an alarm priority according to the alarm confidence. Moreover, continuous updating of the false alarm probability of the alarm can be carried out, so as to improve an accuracy of the false alarm probability, the alarm confidence and the alarm priority continuously. In the above way, for example, correct alarms are displayed as much as possible while false alarms are removed in a limited alarm display area, and a variety of defects that an alarm priority is determined only according to alarm levels in the prior art (such as a waste of clinical resources, fatigue of a medical staff to the alarm and a potential risk faced by a patient) have been reduced.

Some exemplary embodiments have been described in the above. However, it should be understood that various modifications may be made thereto. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other implementation also falls within a protection range of the Claims.

What is claimed is:

1. An alarm controlling method for a patient monitor, comprising:
    acquiring false alarm probabilities of a plurality of current alarms, wherein each false alarm probability is a ratio of a false alarm number to a total alarm number for corresponding current alarm type in historical alarm data;
    determining a priority of each current alarm based on at least the false alarm probability of the current alarm;
    determining a display order of each current alarm according to the priority of the current alarm;
    displaying the current alarm in the display order;
    accumulating the current alarm into the total alarm number for each current alarm type in the historical alarm data, and accumulating a current false alarm into the false alarm number for the current alarm type in the historical alarm data when the current alarm is a false alarm, so as to obtain updated historical alarm data; and
    calculating a ratio of the false alarm number to the total alarm number in the updated historical alarm data so as to update the false alarm probability of the current alarm.

2. The alarm controlling method for a patient monitor according to claim 1, further comprising:
    determining an alarm confidence for each current alarm based on the false alarm probability of the current alarm; and
    displaying the alarm confidence of each current alarm.

3. The alarm controlling method for a patient monitor according to claim 1, wherein determining the priority of each current alarm comprises determining the priority based on the false alarm probability of the current alarm and an alarm level assigned to the current alarm type.

4. The alarm controlling method for a patient monitor according to claim 1, wherein the acquiring false alarm probabilities of a plurality of current alarms comprises:
    determining a false alarm probability of one or more first alarms according to a mapping relationship between an alarm occurrence rule and the first alarms and a specific false alarm probability of the first alarms in the historical alarm data.

5. The alarm controlling method for a patient monitor according to claim 4, wherein the alarm occurrence rule comprises:
    at least two second alarms occur within a specific time interval, the second alarms and the first alarms having the same or different types.

6. The alarm controlling method for a patient monitor according to claim 4, further comprising:
    accumulating a first alarm mapped by the alarm occurrence rule into the historical alarm data, and accumulating a first false alarm into the historical alarm data when the first alarm is the first false alarm, so as to obtain updated historical alarm data;
    calculating a ratio of times of a first false alarm occurring along with the alarm occurrence rule to times of a first alarm occurring along with the alarm occurrence rule in the updated historical alarm data, so as to update a false alarm probability of the first alarm.

7. A self-adaptive alarming method for a patient monitor, comprising:
    accumulating total alarm times and false alarm times of a current alarm into a historical total alarm number and a historical false alarm number in historical alarm data respectively so as to obtain updated historical alarm data;
    acquiring a false alarm probability of the current alarm in the updated historical alarm data which is a ratio of the historical false alarm number to the historical total alarm number of the current alarm;
    determining a priority of the current alarm based on at least the false alarm probability of the current alarm when the current alarm occurs again;
    determining a display order for the current alarm according to the priority of the current alarm;
    displaying the current alarm in the display order;
    accumulating the current alarm into the total alarm number for each current alarm type in the historical alarm data, and accumulating a current false alarm into the false alarm number for the current alarm type in the historical alarm data when the current alarm is a false alarm, so as to obtain updated historical alarm data; and
    calculating a ratio of the false alarm number to the total alarm number in the updated historical alarm data so as to update the false alarm probability of the current alarm.

8. The self-adaptive alarming method for a patient monitor according to claim 7, wherein the acquiring a false alarm probability of the current alarm in the updated historical alarm data according to a ratio of the historical false alarm number to the historical total alarm number of the current alarm comprises:
    if the current alarm conforms to a specific alarm occurrence rule, acquiring the historical total alarm number and the historical false alarm number of the current alarm which conforms to the specific alarm occurrence rule in the updated historical alarm data; and
    calculating a ratio of the historical false alarm number to the historical total alarm number of the current alarm which conforms to the specific alarm occurrence rule, so as to acquire the false alarm probability of the current alarm which conforms to the specific alarm occurrence rule.

9. An alarm controlling apparatus for a patient monitor, comprising:
a processor configured to:
acquire false alarm probabilities of a plurality of current alarms, wherein each false alarm probability is a ratio of a false alarm number to a total alarm number for corresponding current alarm type in historical alarm data;
determine a priority of each current alarm based on at least the false alarm probability of the current alarm; and
determine a display order of each current alarm according to the priority of the current alarm;
accumulate the current alarm into the total alarm number for each current alarm type in the historical alarm data, and accumulate a current false alarm into the false alarm number for the current alarm type in the historical alarm data when the current alarm is a false alarm, so as to obtain updated historical alarm data; and
calculate a ratio of the false alarm number to the total alarm number in the updated historical alarm data so as to update the false alarm probability of the current alarm; and
a display configured to display the current alarm in the display order.

10. The alarm controlling apparatus for a patient monitor according to claim 9, wherein the processor is further configured to determine an alarm confidence for each current alarm based on the false alarm probability of the current alarm, and the display is further configured to display the alarm confidence of the current alarm.

11. The alarm controlling apparatus for a patient monitor according to claim 9, wherein the processor is configured to determine the priority of each current alarm based on the false alarm probability of the current alarm and an alarm level assigned to the current alarm type.

12. The alarm controlling apparatus for a patient monitor according to claim 9, wherein the processor is further configured to:
determine a false alarm probability of one or more first alarms according to a mapping relationship between an alarm occurrence rule and the first alarms and the false alarm probability of the first alarms in historical alarm data.

13. The alarm controlling apparatus for a patient monitor according to claim 12, wherein the alarm occurrence rule comprises:
at least two second alarms occur within a specific time interval, the second alarms and the first alarm having the same or different types.

14. The alarm controlling apparatus for a patient monitor according to claim 12, wherein the processor is further configured to:
accumulate a first alarm mapped by the alarm occurrence rule into the historical alarm data, and accumulate a first false alarm into the historical alarm data when the first alarm is the first false alarm, so as to obtain updated historical alarm data; and
calculate a ratio of times of a first false alarm occurring along with the alarm occurrence rule to times of a first alarm occurring along with the alarm occurrence rule in the updated historical alarm data, so as to update a false alarm probability of the first alarm.

15. The alarm controlling apparatus for a patient monitor according to claim 9, wherein the alarm controlling apparatus for a patient monitor is provided in a patient monitor or in a workstation connected to the patient monitor;
when the alarm controlling apparatus for a patient monitor is provided in the workstation, the processor is configured to acquire the false alarm probabilities of the plurality of current alarms from a plurality of patient monitors.

* * * * *